United States Patent

Ingels

Patent Number: 6,000,941
Date of Patent: Dec. 14, 1999

[54] SEPARABLE ORTHODONTIC PLIERS

[76] Inventor: Luis Ingels, 1828 Evergreen St., Duarte, Calif. 91010

[21] Appl. No.: 09/193,988

[22] Filed: Nov. 18, 1998

[51] Int. Cl.⁶ ........................................... A61C 3/14
[52] U.S. Cl. ................................. 433/159; 433/4
[58] Field of Search ........................ 433/4, 159

[56] References Cited

U.S. PATENT DOCUMENTS

| | | | |
|---|---|---|---|
| 2,352,808 | 7/1944 | Siqveland | 433/159 |
| 3,105,402 | 10/1963 | Tofflemire | 433/159 |
| 4,392,494 | 7/1983 | Ashby | 433/4 |
| 5,197,879 | 3/1993 | Fowler, III et al. | 433/4 |
| 5,232,360 | 8/1993 | Ingels | 433/4 |

*Primary Examiner*—John J. Wilson
*Attorney, Agent, or Firm*—Donald D. Mon

[57] ABSTRACT

A separable pliers having a pair of arms separably hinged together. They may be separated only when the handles are far enough apart. A lip on one handle, and a hook on a bias spring integral with the other handle engage one another to restrain the handles from opening that far unless and until the spring is bent to release the hook from the lip, after which the arms can be separated.

5 Claims, 4 Drawing Sheets

SEPARABLE ORTHODONTIC PLIERS

FIELD OF THE INVENTION

A two piece orthodontic pliers whose parts are separable, and are restricted from separation by the same spring which biases the handles of the pliers apart from one another.

BACKGROUND OF THE INVENTION

Orthodontic pliers which include two separable parts are well known. Each one of two parts has a handle and some type of jaw device. The parts are joined by a hinge which must be disassembled to separate the parts. The ultimate objective is to provide a strong and reliable pliers construction which wears well, and whose parts are amenable to simple cleaning and sterilization procedures. Uncomplicated procedures and physical arrangements for hinge separation are much to be preferred.

Examples of known separable pliers are Fowler III U.S. Pat. No. 5,197,879 and Ingels U.S. Pat. No. 5,232,360. The Fowler pliers illustrate the problems when a pinless hinge is used. It relies on a dovetail arrangement that holds the parts together throughout a pre-established amount of opening of the handles and jaws. Beyond that limit, the parts fall apart from one another. Either some releasable means must be provided to limit this movement, or care must be taken by the user to prevent movement beyond the limit. The relatively short dovetail surfaces take the wear caused by squeezing of the handles together. Ultimately this wear will cause undesirable sloppiness of action, or some adjustment means must be provided.

The Ingels patent provides a hinge that has a pin and a recess which both center the parts and take the wear over a substantial area. The parts are prevented from separating by overhanging shoulders of limited extent, and readily separate when their handles are separated beyond this extent, but are held by an extra spring.

It is an object of this invention to provide a separable pliers in which the separation of the handles is limited by the same spring which biases the handle apart. This provides a pliers which is reliably held together and which can readily be disassembled by the simple deflection of the spring.

BRIEF DESCRIPTION OF THE INVENTION

A separable orthodontic pliers according to this invention includes a first part and a second part. Each part includes a handle, a jaw member, and a hinge portion between them. The hinge portion on one part is a cylindrical pin having a peripheral bearing wall. The hinge portion of the other part is a bore with a peripheral bearing wall. The bearing walls have substantially the same diameter so as to make a close rotational fit with one another.

One of said parts includes a lip spaced from its handle and facing toward its hinge portion. The other of said parts includes an integral flexible spring arm, extending away from it toward said lip. Said spring arm has at its free end a hook so disposed and arranged as to engage the lip when the handles are at their maximum permissible spacing apart without risk of separation.

The spring arm is formed so as to bear against the lip to bias the handles apart. Separation is enabled by deflecting the spring arm so its hook passes the lip and the overhangs no longer interfere with the separation of the parts.

The above and other features of this invention will be fully understood from the following detailed description and the accompanying drawings, in which:

DETAILED DESCRIPTION OF THE INVENTION

Figure 1:
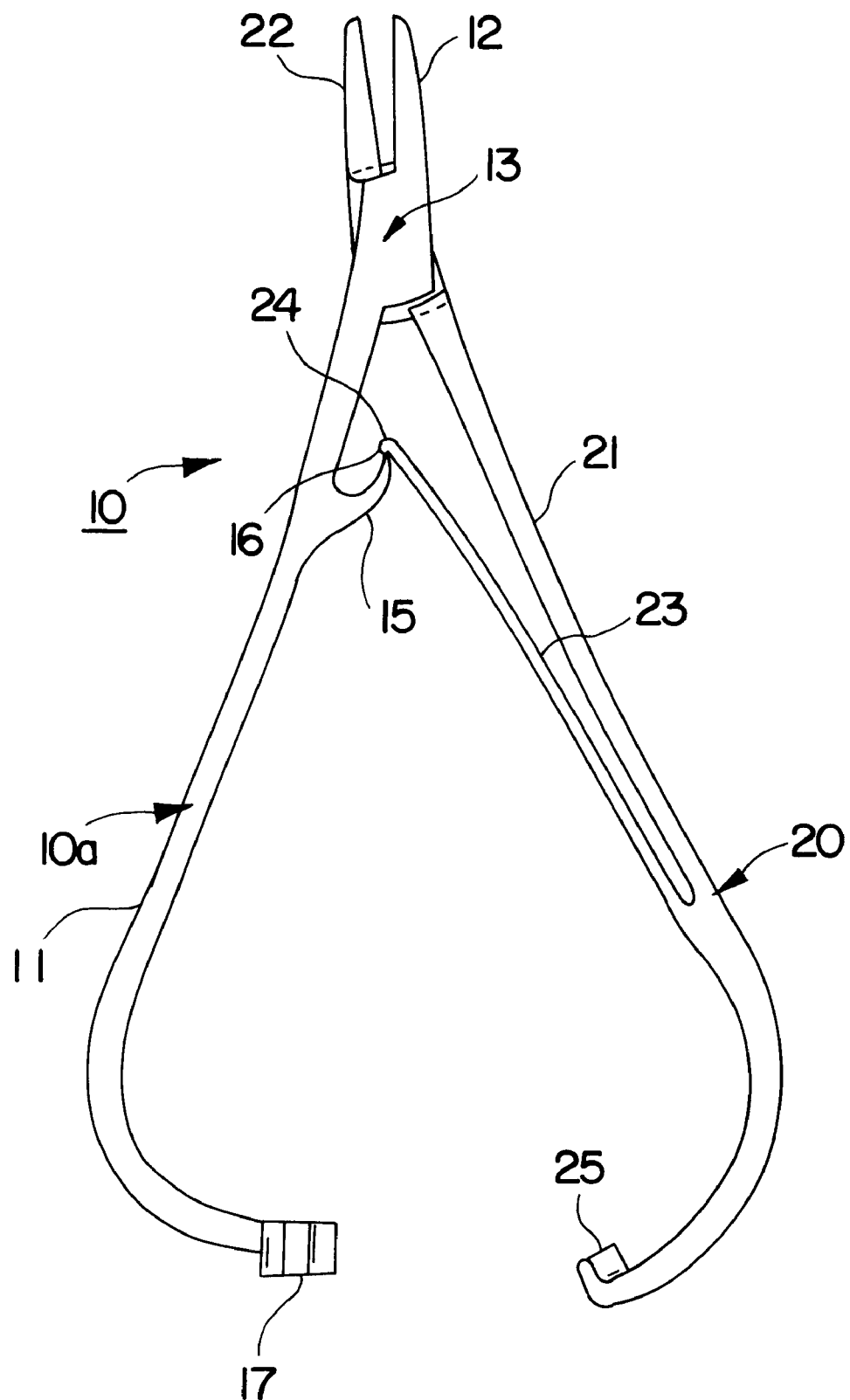
FIG. 1 is a plan view of the presently preferred embodiment of the pliers in its repose, ready to use condition.

A separable orthodontic pliers 10 is shown in FIG. 1 in its repose condition, which is the maximum opening permitted without release of the hinge. There is no risk of separation at this position. First part 10a has a handle 11 and a jaw 12 on opposite sides of a hinge 13. It further includes a lip 15 formed as an integral extension of the handle. The lip has a tip 16 that is spaced from the handle. At its free end a group of ratchet notches 17 are formed for a purpose to be disclosed.

Second part 20 has a handle 21 and a jaw 22 on opposite sides of hinge 13. It further includes an integral spring arm 23 that extends from the handle in the direction of the hinge. The spring arm is stiffly springly flexible. At its end it forms a hook 24 which in the position of FIG. 1 engages the lip and prevents further pivoting apart of the handles unless this engagement is released. At its free end a ratchet tooth 25 is formed which can releasably engage in ratchet notches 17 to hold the handles in an adjustably closed position relative to one another.

The details of the hinge are shown in FIG. 4–7. First part 10a (FIG. 4) includes a pin 30 with a cylindrical peripheral bearing surface 31 having a diameter. It extends from a flat surface 32 which has at its edge two arcuate blades 33, 34 having top and bottom surfaces 35, 36. The blades are centered on the hinge center 37.

Second part 20 (FIG. 6) has a bore 40 having a peripheral cylindrical bearing surface 41 with a diameter. The diameters of the bearing surfaces are substantially equal, permitting a close rotational fit which takes most of the wear when the handles are squeezed together.

A pair of undercut grooves 42, 43 are formed, each centered on the hinge axis. Each has an overhanging ledge 44. These have about the same arcuate extent as the blades. The grooves have about the same thickness as the blades so as to hold the handles in precise alignment.

It will now be seen that with the handles spread apart and the hook and lip disengaged, the parts can be pressed together, inserting the pin into the bore. Then, rotating the handles, moving them toward each other, the blades enter the grooves and the parts are held together.

Figure 2:
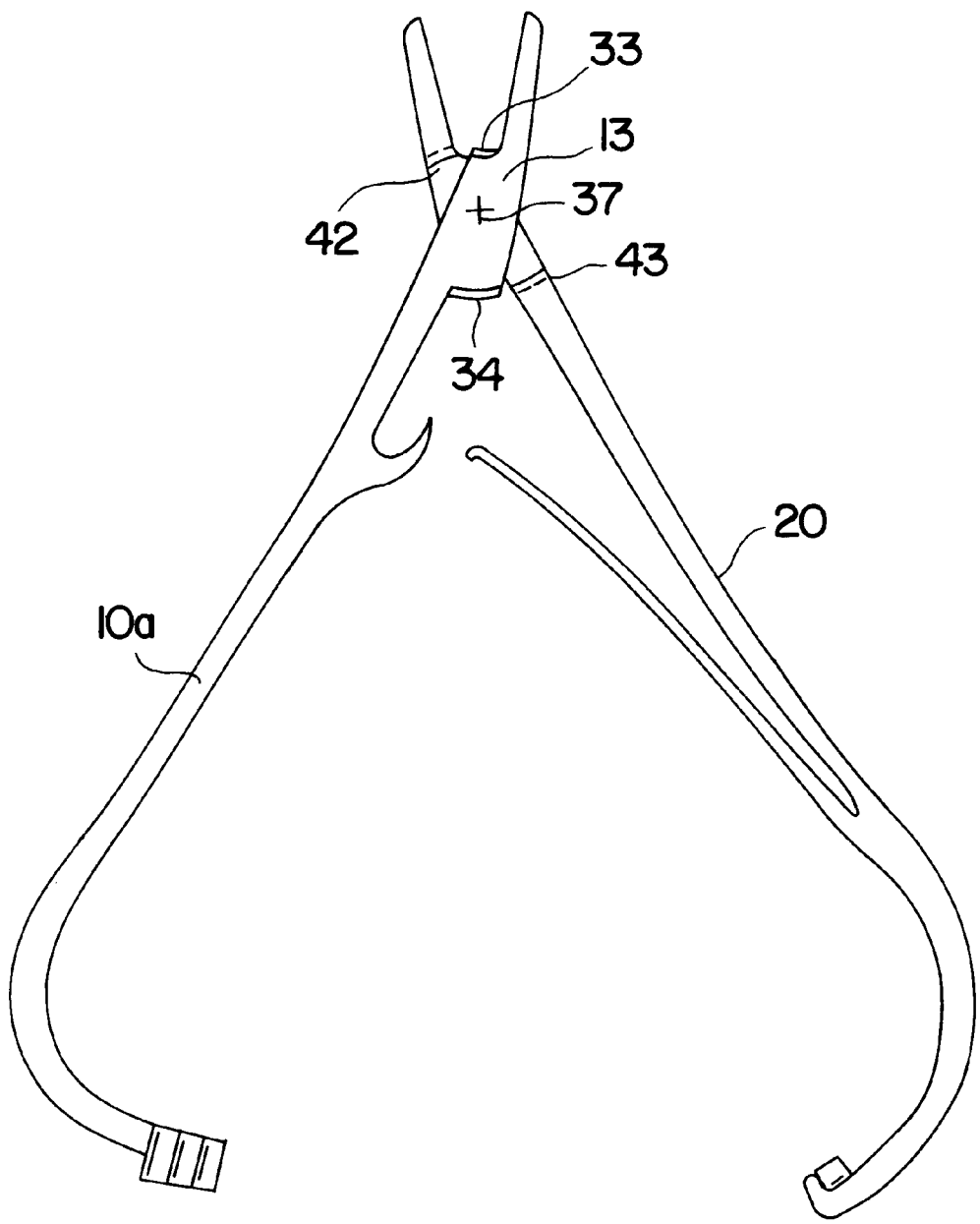
FIG. 2 is a view similar to FIG. 1 with the pliers in a condition to be assembled or disassembled.
Figure 3:
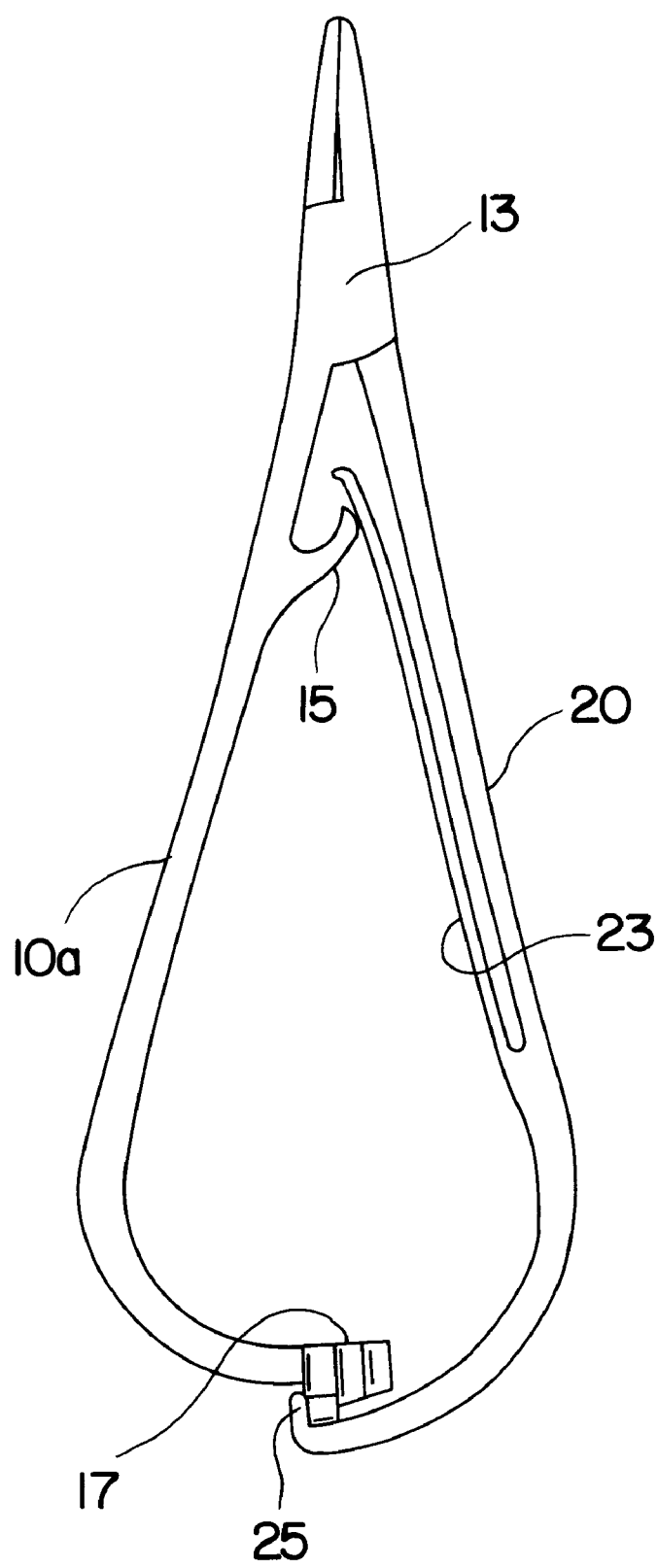
FIG. 3 is a similar view showing the pliers closed and latched.
Figure 4:
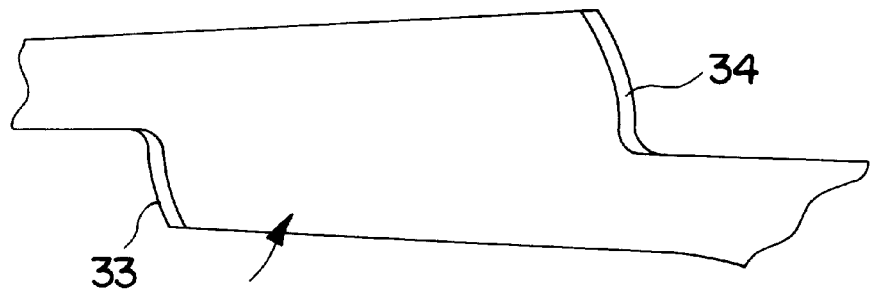
FIG. 4 is a fragmentary plan view of one of the parts.
Figure 5:
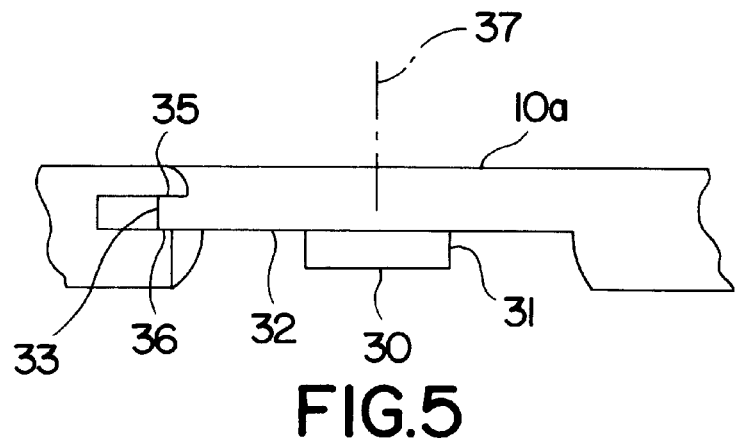
FIG. 5 is a bottom view of FIG. 4.
Figure 6:
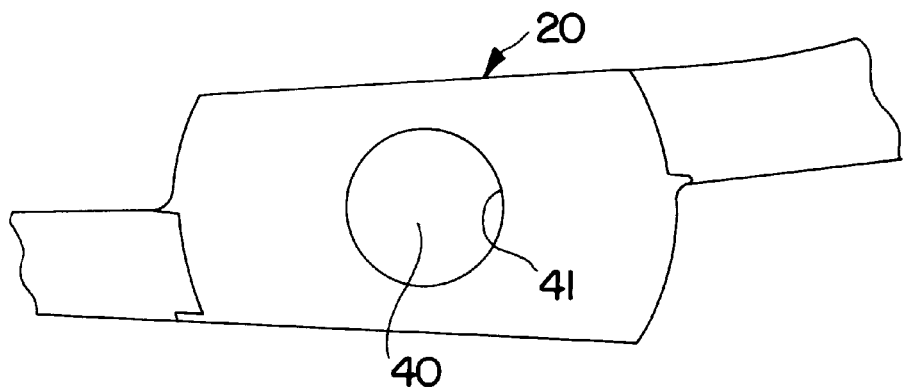
FIG. 6 is a fragmentary plan view of the other of the parts.
Figure 7:
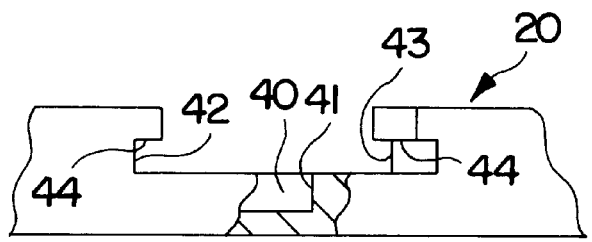
FIG. 7 is a bottom view of FIG. 6.

Now attention is called to FIGS. 2 and 3. In FIG. 2, the parts have just been put together as described. Notice that the blades are not yet in the grooves, nor is the spring arm in contact with the pin. The illustrated position of the spring arm assures a prevailing bias.

FIG. 3 shows the fully closed position of the pliers. The blades and grooves are fully engaged, as are the ratchet teeth and notches. Attention is called to the spring arm. Notice that it has been deflected toward its own handle by contact with the lip. This biases the handles apart. When the ratchet is released by deflecting the ends of the handles, the spring bias will tend to separate the handles for the user's convenience.

FIG. 1 shows the pliers in the unlatched, fully assembled condition, ready for use. The spring arm has biased the handles apart to the maximum extent permitted without bending (deflecting) the spring arm. The hook has engaged the lip, which prevents further separation of the handles. This is a continuing bias useful to the user, and which also strengthens the grip of the hook on the lip. Notice in FIG. 1 that the blades are still in the grooves to an extent sufficient to prevent separation of the handles.

The handles may be separated by bending the spring arm inwardly to clear the tip 16 of lip 15, permitting separation as shown in FIG. 2. The parts may then be separated by removing the pin from the bore. The blades clear the grooves in this position. Reassembly of the pliers requires no more than again plugging the pin into the bore and moving the handles toward one another to engage the blades in the grooves. The hook and lip will be engaged, and the pliers is ready for use.

Simple jaws are shown on the parts. Any other desired jaw means may be used instead and for any desired purpose.

The parts of the pliers are preferably made of a single piece of metal, usually of stainless steel. The shapes shown are readily made on conventional machinery, and can effectively be cleaned and sterilized.

The construction shown is convenient for a user such as an orthodontist, providing good spring bias and locking over a wide range of opening, reliable assembly, and long wear.

This invention is not to be limited by the embodiment shown in the drawings and described in the description, which is given by way of example and not of limitation, but only in accordance with the scope of the appended claims.

I claim:

1. Separable pliers comprising:

a first and a second part, each part having a handle and a jaw, and a hinge portion between its respective handle and jaw;

a pair of arcuate blades on one of said parts, and a pair of arcuate grooves on the other of said parts, said blades and grooves being concentric and of limited arcuate length, whereby said blades are engaged in said grooves in a limited extent of separation of said handles, and disengaged beyond said limited extent;

said hinge portion of one of said parts being a pin having a cylindrical peripheral bearing wall with an axis;

said hinge portion of the other of said parts being a bore having a peripheral bearing wall, said bearing walls being close fitting and concentric, said blades and grooves being concentric with said bearing walls;

a lip on one of said handles spaced from its respective handle, facing the other handle, a spring arm on and extending from the other handle, extending toward said hinge and toward said one handle, and a hook on said spring arm so disposed and arranged as to engage said lip and prevent further separation of said handles until and unless said spring arm is bent to release said hook from said lip.

2. Separable pliers according to claim 1 in which said lip and said spring arm are integral with their respective handles.

3. Separable pliers according to claim 1 in which said groove is formed with an overhanging shoulder that engages said blade to prevent their separation when engaged.

4. Separable pliers according to claim 3 in which said lip and said spring arm are integral with their respective handles.

5. Separable pliers according to claim 4 in which said spring arm is blade-like, and in which said hook comprises a curved tip to engage said lip.

\* \* \* \* \*